United States Patent [19]

Scott

[11] Patent Number: 4,594,351
[45] Date of Patent: Jun. 10, 1986

[54] FURAN OR THIOPHENE DERIVATIVES OF IMINOMETHYL PIPERIDINES AND USE TO INHIBIT GASTRIC SECRETION

[75] Inventor: Malcolm K. Scott, Ambler, Pa.

[73] Assignee: McNeilab, Inc., Fort Washington, Pa.

[21] Appl. No.: 727,040

[22] Filed: Apr. 25, 1985

Related U.S. Application Data

[62] Division of Ser. No. 540,265, Oct. 11, 1983, Pat. No. 4,528,293.

[51] Int. Cl.$^4$ ............... C07D 405/12; C07D 417/12; A61K 31/445
[52] U.S. Cl. .................... 514/320; 514/324; 514/326; 546/196; 546/202; 546/213; 546/214
[58] Field of Search ............... 546/214, 196, 213, 202; 514/326, 320, 324

[56] References Cited
U.S. PATENT DOCUMENTS 4,370,335  1/1983  Scott .................. 514/331

Primary Examiner—Henry R. Jiles
Assistant Examiner—Dale A. Bjorkman
Attorney, Agent, or Firm—David J. Levy

[57] ABSTRACT

Compounds of the following formula (I):

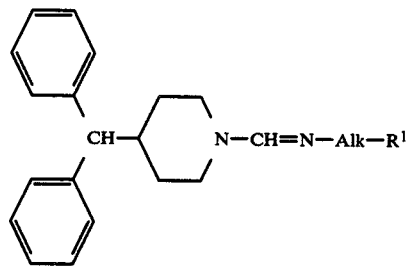

wherein Alk is a straight or branched chain alkylene of about 1 to 12 carbons and $R^1$ is a heterocyclic ring system, have been found to possess potent antisecretory activity and are thus useful in the treatment of hyperacidity.

17 Claims, No Drawings

FURAN OR THIOPHENE DERIVATIVES OF IMINOMETHYL PIPERIDINES AND USE TO INHIBIT GASTRIC SECRETION

The present application is a division of U.S. Ser. No. 540,265 filed Oct. 11, 1983, now U.S. Pat. No. 4,528,293.

Various 1-iminomethyl piperidines are described in U.S. Pat. Nos. 4,251,655 and 4,370,335 including 4-diphenylmethyl-1-(octylimino)methyl piperidine and 4-diphenylmethyl-1-(oxoalkyl)iminomethyl piperidines, respectively.

SUMMARY OF THE INVENTION

The present invention comprises various heterocyclic alkyl derivatives of 4-diphenylmethyl piperidines of the following formula (I):

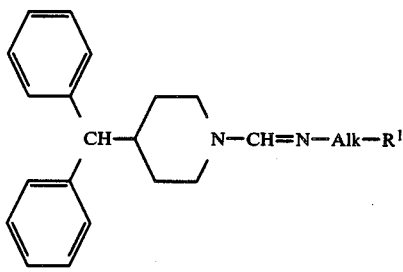

(I)

wherein Alk is an alkylene unit of about 1 to 12 carbons and $R^1$ is a heterocyclic group which may have various substitions as described herein as well as salts of such derivatives. Also, part of the present invention are pharmaceutical compositions and methods for the treatment of individuals having hyperacidity in their gastric tract.

DETAILED DESCRIPTION OF THE INVENTION

The piperidine derivatives of the invention are 4-diphenylmethyl-1-iminomethylpiperidines of the following formula (I):

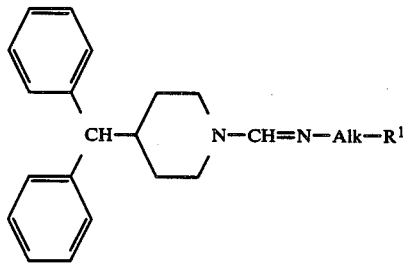

(I)

wherein

Alk is divalent straight or branched chain alkylene group of about 1 to 12 carbons; and $R^1$ is a heterocyclic group selected from the group consisting of furan, benzofuran, thiophene, benzothiophene, pyrrole, indole, pyridine, quinoline or isoquinoline, which heterocyclic group may be optionally substituted:

(i) on a 6-membered ring carbon thereof by one or two substituents selected from the group consisting of alkyl, alkoxy, alkylthio, hydroxy, mercapto, nitro, amino, alkylamino, dialkylamino, trifluoromethyl, alkanoylamino, halo, carboxy, carbamoyl or alkoxycarbonyl;

(ii) on adjacent ring carbons of the phenyl ring of the benzofuran, benzothiophene, quinoline or isoquinoline rings by a methylenedioxy group;

(iii) on the nitrogen atom of the pyrrole or indole rings by alkyl, phenyl, or phenylalkyl; and (iv) on a carbon atom of a 5-membered ring thereof by one or two substituents selected from the group consisting of alkyl, carboxy or phenyl; and the pharmaceutically-acceptable salts thereof.

Alk in more detail is an alkylene unit of about 1 to 12 carbons e.g. about 1 to 6 carbons, which includes branched chain alkylene. Examples are methylene, ethylene, trimethylene, tetramethylene, —CH₂CH(CH₃)CH(CH₃)CH₂—, and reading from left to right with the imine nitrogen joined at the left, —CH₂CH₂CH(CH₂CH₃)CH₂—, —CH₂CH(CH₂CH(CH₃)₂)— and —CH₂CH(CH(CH₃)₂)CH₂CH₂—. Preferably, the alkylene is of 1 to 5 carbons in a straight chain backbone with 0 to 2 alkyl substituents of 1 to 3 carbons each.

In more detail, $R^1$ may be a 2- or 3-furanyl; a 2-, 3-, 4-, 5-, 6- or 7-benzofuranyl; a 2- or 3-thiopheno; a 2-, 3-, 4-, 5-, 6- or 7-benzothiopheno; a 1-, 2- or 3-pyrrolo; a 1-, 2-, 3-, 4-, 5-, 6- or 7-indolo; a 2-, 3- or 4-pyridino; a 2-, 3-, 4-, 5-, 6-, 7- or 8-quinolino; or a 1-, 3-, 4-, 5-, 6-, 7- or 8-isoquinolino group. In particular, the $R^1$ group may be attached to the —Alk— group by a ring carbon, e.g., other than attachment at the 1-position.

The $R^1$ moiety may be an unsubstituted heterocycle or it may be substituted by one or more of the substituents classified as (i), (ii), (iii) and (iv) above, in particular, by a single substituent. The alkyl portions of the alkyl, alkoxy, alkylthio, alkylamino, dialkylamino, alkoxycarbonyl and phenylalkyl substituents may contain about 1 to 6 carbons each, e.g., methyl (or methylene for phenylalkyl), ethyl, iso- or n-propyl, n-, sec-, iso- or t-butyl and the isomers of pentyl and hexyl, e.g., methyl, methoxy, ethylthio, ethylamino, dimethylamino, n-butoxycarbonyl and benzyl. The alkanoyl portion of the alkanoylamino substituent may contain about 2 to 8 carbons, e.g., N-acetylamino or 2-methylpropanoylamino. The halo group may be fluoro, chloro, bromo or iodo. Particular $R^1$ groups are 2-furanyl, 3-1H-indolyl, 1-methyl-1H-pyrrol-2-yl, 2-thiopheno, 2-pyridinyl and 4-pyridinyl.

The salts of compounds of formula (I) are normally acid-addition salts although if $R^1$ is substituted by a carboxy group, the salt may be a base-addition salt thereof, e.g., by reaction with an alkali metal hydroxide to form a salt such as a sodium salt. The acid addition salts are formed by reaction of an amidine of formula (I) with an inorganic or organic acid such as a hydrohalic acid, e.g., hydrochloric, hydrobromic or hydroiodic acid, a mineral acid, e.g., sulfuric, nitric acid or phosphoric acid, or an organic acid such as acetic, propionic, glycolic, pamoic, pyruvic, oxalic, malonic, succinic, maleic, fumaric, malic, tartaric, citric, benzoic, cinnamic, mandelic, methanesulfonic, ethanesulfonic, benzenesulfonic, p-toluenesulfonic, salicylic, 2-naphthalene-sulfonic or p-aminosalicylic acid.

Compounds of Formula (I) may exist in various isomeric forms, e.g., in view of the presence of an asymmetric carbon. It is understood that the present invention includes all such individual isomers and their racemates. Also within the scope of the invention are compounds of the invention in the form of hydrates and other solvate forms.

The compounds of the invention of formula (I) may be prepared by the procedure described by C. A. Buehler and D. E. Pearson in "Survey of Organic Syntheses" at pages 900–901, Wiley-Interscience, New York (1970). The procedure comprises reacting 4-diphenylmethylpiperidine available from Reilly Tar and Chemical of Indianapolis, Ind. 46204, with acetic formic anhydride, the anhydride preferably being present in excess. The piperidine and anhydride are combined with cooling and are allowed to stir for about 18 hours. The resulting reaction mixture dissolved in an organic solvent such as, for example, a halocarbon e.g., carbon tetrachloride, chloroform, 1,2-dichloroethane, and the like, an aromatic hydrocarbon e.g., benzene, xylene, toluene, and the like is then treated with an aqueous solution of a weak base e.g., sodium bicarbonate, until the aqueous layer is neutral. The organic layer is separated and any solvent present is removed to obtain the intermediate N-formyl-4-(diphenylmethyl)piperidine. The N-formyl intermediate is then treated either neat or in the presence of an organic solvent such as, for example, a halocarbon, e.g., $CHCl_3$, $CH_2Cl_2$ or a hydrocarbon e.g., benzene or toluene, at 25° to 100° C. with a suitable activating agent selected from, for example, phosgene, $(CH_3)_3O^+BF_4^-$, $(C_2H_5)_3O^+BF_4^-$, $(CH_3O)_2SO_2$, $CH_3OSO_2F$, $POCl_3$, $PCl_5$ and the like, for about one-half to three hours, to produce the activated formamide after which the reaction mixture is allowed to cool. Addition of the appropriate primary amine of the formula $H_2N$—Alk—$R^1$ yields the desired product of formula (I) which may be isolated and purified by techniques known in the art, e.g., by stripping off the solvent and recrystallizing the desired product in the free base or acid addition salt form.

Compounds of the formula $H_2N$—Alk—$R^1$ are known in the art, e.g., as described in U.S. Pat. Nos. 3,723,441; 3,767,659; 3,978,066; and 4,238,487. In addition, various compounds of the formula $H_2N$—Alk—$R^1$ can be made from another compound within the same formula as known in the art. A compound with an alkoxy or alkylthio substituent can be prepared from one with the corresponding hydroxy or mercapto group by treatment with sodium hydroxide to prepare the sodium salt and reaction of the salt with an alkyl iodide to prepare the alkoxy or alkylthio group. An amino group substituent can be prepared from the corresponding nitro compound by reduction with a reducing agent such as Zn and HCl or palladium and hydrogen. From the amino compound, the corresponding alkylamino compound may be prepared by reductive alkylation with an aldehyde such as formaldehyde to yield a $CH_3$ group, or acetaldehyde, to yield an ethyl group when followed by reduction with hydrogen in the presence of a catalyst such as palladium. Repeating this process yields the dialkylamino compound. The alkanoylamino compound may be prepared from the amino compound by the Schotten-Bauman reaction with an acid chloride. From the carboxy compound, the corresponding ester is prepared by reaction with the appropriate alcohol with an acid catalyst such as sulfuric acid. The ester may be used to prepare the carbamoyl compound by reaction with $NH_3$ at an elevated temperature and pressure. The methylenedioxy may be prepared by reacting the corresponding dihydroxy compound with formalin. Pyrroles substituted on the nitrogen atom may be prepared by reaction of 2,5-dimethoxytetrahydrofuran with the appropriate alkylamine or with aniline or phenylalkylamine. Pyrroles of the formula $H_2N$—Alk—$R^1$ wherein $R^1$ is a pyrrole ring and Alk contains at least 2 carbons in the chain directly linking $NH_2$ and $R^1$ may be prepared by the method of A. J. Castro et.al. described in the Journal of Organic Chemistry, Vol. 30, pages 344–350 (1965). In addition, an N-substituted 2-formyl pyrrole may be prepared as described by Elming et al in Acta Chim. Scand., Vol. 6, pages 867–874 (1952) which aldehyde may then be elaborated to produce the aminoalkyl sidechain, e.g., by reaction with a Wittig reagent prepared from Br-alkyl-CN wherein the carbons of the CHO, alkyl and CN group will form the Alk group in the final product of formula (I). After the Wittig reaction the resultant double bond and cyano groups may be reduced as known in the art, e.g., by a first reduction with a noble metal and hydrogen and a second reduction of the cyano group with lithium aluminum hydride.

The compounds of the invention of formula (I) are useful for the inhibition of gastric acid secretion as measured by the following test. Female Sprague-Dawley rats are fasted twenty-four hours before testing and are given water ad libidum while being kept in individual cages. On the day of testing, the rats are weighed within a range of ±20 grams.

Surgery is carried out under light ether anesthesia. As soon as the rat is anesthetized its teeth are removed and a mid-line incision is made on the abdomen about 1½ inches in length and the stomach and duodenum are exposed. If at this point the stomach is filled with food or fecal material, the rat is discarded. If the condition of the stomach is acceptable, a purse string stitch is placed on the fundic portion of the stomach with a suture, taking care not to pierce any blood vessels in the area. A small nick is then made into the stomach in the center of the purse string, and a cannula, consisting of a small vinyl tube with a flange on one end, is put into the stomach, and the purse string stitch is closed tightly around the flange. The test compound is administered either intraduodonally (i.d.) immediately after surgery or orally (p.o.) one hour prior to surgery at doses generally ranging from about 0.25 to about 160 mg/kg in a volume of 0.5 ml/100 grams rat. Control rats receive the test vehicle, 0.5% aqueous hydroxypropyl methyl cellulose.

After surgery and, in the case of i.d. administration, after administration of the test compound, the abdominal wall and skin are closed simultaneously with three or four 18 mm wound clips and a collecting tube is placed on the cannula. Each rat is then placed in a box in which a longitudinal slit has been made to allow the cannula to hang freely and to allow the rat to move about unencumbered. After the rat has been allowed to stabilize for thirty minutes, the collection tube on the cannula is discarded and replaced with a clean tube to receive the gastric juice. Collections are made one hour after stabilization.

The sample of gastric contents collected is drained into a centrifuge tube and centrifuged to pack down the sediment. The volume is read and a 1 ml aliquot of the supernatant is put into a beaker containing 20 ml of distilled water and is titrated to pH7 using 0.01N sodium hydroxide. Results are determined for Volume, Titratable Acid and Total Acid Output, where Volume equals total ml of gastric juice minus sediment; Titratable Acid (meq/1) equals amount of 0.01N sodium hydroxide needed to titrate the acid to pH7; and Total Acid Output equals Titratable Acid times Volume. Results are reported as the $ED_{50}$ dose (mg/kg required to produce an average of 50% inhibition in Total Acid Output versus controls in the animals tested for a particular compound) and as percent inhibition. The exemplified compounds of the invention all demonstrate a significant inhibition both i.d. and p.o. at less than 80 mg/kg, with preferred compounds having an $ED_{50}$ p.o. less than 20 mg/kg.

The pharmacological effects of compounds of the present invention as inhibitors of gastric acid secretion is shown in Table I below:

TABLE I

| —Alk—$R^1$ | Example No. | $ED_{50}$ Acute Gastric Fistula (mg/kg, p.o.) |
|---|---|---|
| —$CH_2$—(2-furanyl) | 1 | 6.91 |
| —$(CH_2)_2$—(1H-indol-3-yl) | 2 | 4.34* |
| —$(CH_2)_2$—(1-methylpyrrol-2-yl) | 3 | 3.61 |
| —$CH_2$—(2-thienyl) | 4 | 6.59 |
| —$(CH_2)_2$—(2-pyridyl) | 5 | 3.47 |
| —$(CH_2)_2$—(4-pyridyl) | 6 | 18.83 |

*compound administered intraperitoneally

It is well-known that excessive secretion of gastric hydrochloric acid leads to unneeded peptic activity and endangers the mucous lining of the duodenum. The use of gastric antisecretory agents is thus desirable as an aid in the prevention and amelioration of distress occasioned by high concentrations of gastric acid.

In view of the antisecretory activity of the subject compounds, there is further provided herein a method of inhibiting gastric acid secretion which comprises internally administering to a subject (man or other animal) an effective gastric acid secretion inhibiting amount of a compound of formula (I), in base or acid or base addition salt form, preferably in admixture with a pharmaceutically acceptable diluent or carrier. If an acid addition salt form is used, said salt must of course be pharmaceutically-acceptable and non-toxic. Pharmaceutical compositions comprising a subject compound (I) are also considered a further aspect of the present invention.

To prepare the pharmaceutical compositions of the present invention, a compound of formula (I) or an acid addition salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. The compounds of the invention may be administered to a man or other animal in need of an antisecretory agent to inhibit gastric acid secretion in an amount of about 0.25 to 5 mg/kg of body weight per day, preferably about 0.5 to 3 mg/kg, which dosage may be divided into 2 to 4 doses. The pharmaceutical compositions herein will contain, per dosage unit, e.g., tablet, capsule, powder, injection, teaspoonful, and the like, from about ten to about five hundred milligrams of the active ingredient, and preferably from about fifteen to about two hundred fifty milligrams.

In the following Examples and throughout the specification, the following abbreviations are used: mg (milligrams); kg (kilograms); N (normal); ml (milliliters); l (liters); meq (milliequivalents); g (grams); °C. (degrees centigrade); E (trans); Z (cis); mp (melting point); and C,N,H,O, etc. (the chemical symbols for the elements).

EXAMPLE 1

4-(Diphenylmethyl)-1-[(2-furanylmethyl)imino methyl]piperidine (E)-2-butenedioate (1:1) hydrate (5:2)

N-Formyl-4-diphenylmethylpiperidine: A solution of 18.70 g (17.3 ml; 0.183 mole) of acetic anhydride and 10.05 g (8.77 ml; 0.22 mole) of 97% formic acid was stirred at 25° C. for two hours. The solution was cooled in ice and 22.0 g (0.088 mole) of 4-diphenylmethylpiperidine was added portionwise. The resulting mixture was stirred at 25° C. overnight. Diethylether and a small amount of $CHCl_3$ were added and the solution treated with a saturated sodium bicarbonate solution until basic. The organic layer was separated, dried over $K_2CO_3$, filtered and evaporated. The yellow oily residue was dissolved in an equal volume of ethanol and cooled. Filtration afforded 17.3 g (71%) of a white crystalline solid, mp 128°-130° C. Recrystallization from ethanol gave a solid mp 131°-134° C.

Elemental Analysis: Calculated for $C_{19}H_{21}NO$: C, 81.67; H, 7.59; N, 5.01; Found: C, 81.65; H, 7.62; N, 4.98.

A solution of 10.0 g (0.038 mole) of N-formyl-4-diphenylmethylpiperidine in 70 ml of methylene chloride was treated with phosgene until gas evolution ceased. The reaction mixture was evaporated, more methylene chloride was added and evaporated, and the residue dissolved in 70 ml of methylene chloride. Furfurylamine, 3.48 g (0.036 mole), in 10 ml of methylene chloride was added at such a rate as to maintain a gentle reflux. The reaction mixture was treated with 3.36 g (4.98 ml, 0.036 mole) of triethylamine and stirred at 25° C. After 4 hours, the reaction was cooled to 0° C. and treated with excess 2N sodium hydroxide solution. The methylene chloride layer was separated, dried over anhydrous potassium carbonate, filtered, and evaporated to yield an oil which was converted to the fumarate salt and recrystallized from a mixture of methanol and ether to yield the title product, a light yellow solid, mp 172°–174° C.

Elemental Analysis: Calculated for $C_{24}H_{26}N_2O.C_4H_4O_4.0.4H_2O$: C, 69.81; H, 6.44; N, 5.82; $H_2O$, 1.50; Found: C, 69.75; H, 6.50; N, 5.81; $H_2O$, 1.69.

EXAMPLE 2

N-(4-Diphenylmethyl-1-piperidinyl)-methylene-3-1H-indoleethaneamine monohydroiodide Following the procedure of Example 1 with the substitution of an equimolar amount of 2-(3-indole)ethaneamine for furfurylamine and hydroiodic acid to prepare the salt, the title compound was prepared, mp 236°–238° C.

Elemental Analysis: Calculated for $C_{29}H_{31}N_3.HI$: C, 63,39; H, 5.89; N, 7.65; Found: C, 63.37; H, 5.88; N, 7.65.

EXAMPLE 3

4-Diphenylmethyl-1-[N-[(1-methyl-1H-pyrrol-2-yl)ethyl]iminomethyl]piperidine (E)-2-butenedioate A mixture of 10.0 g (0.036 mole) of N-formyl-4-diphenylmethylpiperidine and 4.32 g (3.20 ml, 0.036 mole) of dimethylsulfate was heated on a steambath for 3 hours to give a clear thick syrup. This material was dissolved in 40 ml of $CH_2Cl_2$ and cooled to 0° C. A solution of 4.44 g (0.036 mole) of 2-(aminoethyl)-1-methylpyrrole in 25 ml of $CH_2Cl_2$ was added, and the reaction mixture was stirred at 25° C. for 4 hours. The reaction was cooled to 0° C., treated with excess 2N NaOH solution, and the $CH_2Cl_2$ layer was separated and dried over anhydrous $K_2CO_3$. Filtration and evaporation gave a residue which was dissolved in ether, filtered, and evaporated, affording an oil which was converted to the fumarate salt, mp 197.5°–199° C. (after recrystallization from ethanol).

Elemental Analysis: Calculated for $C_{26}H_{31}N_3.C_4H_4O_4$: C, 71.83; H, 7.03; N, 8.38; Found: C, 71.63; H, 7.16; N, 8.42.

EXAMPLE 4

4-(Diphenylmethyl)-1-[(2-thiophenemethyl)imino]methylpiperidine (E)-2-butenedioate (1:1) hydrate (2:1)

The procedure of Example 1 was followed using an equimolar amount of 2-aminomethylthiophene in the place of furfurylamine to obtain the fumarate salt title compound, mp 201°–203° C.

Elemental Analysis: Calculated for $C_{24}H_{26}N_2S.C_4H_4O_4.0.5H_2O$: C, 67.31; H, 6.25; N, 5.61; $H_2O$, 1.80; Found: C, 67.23; H, 6.38; N, 5.56; $H_2O$, 1.98.

EXAMPLE 5

4-(Diphenylmethyl-1[[2-(2-pyridinyl)ethyl]iminomethyl]piperidine (E)-2-butenedioate (1:1)

Following the procedure of Example 1 and substituting an equimolar amount of 2-aminoethylpyridine for furfurylamine, the title compound fumarate salt was obtained, mp 192°–194° C.

Elemental Analysis: Calculated for $C_{26}H_{29}N_3.C_4H_4O_4$: C, 72.13; H, 6.66; N, 8.41; Found: C, 71.90; H, 6.70; N, 8.39.

EXAMPLE 6

4-Diphenylmethyl-1-[[2-(4-pyridinyl)ethyl]iminomethyl]piperidine 2-naphthalenesulfonate hydrate (4:4:3)

The procedure of Example 1 was followed with the substitution of 4-aminoethylpyridine for an equimolar amount of furfurylamine and using 2-naphthalenesulfonic acid as the acid to obtain the title compound, mp 156.5°–158° C.

Elemental Analysis: Calculated for $C_{29}H_{29}N_3.C_{10}H_8SO_3.0.75H_2O$: C, 71.44; H, 6.41; N, 6.94; $H_2O$, 2.23; Found: C, 71.22; H, 6.41; N, 6.94; $H_2O$, 2.55.

What is claimed is:

1. A 4-diphenylmethyl-1-imino-methylpiperidine of the following formula (I):

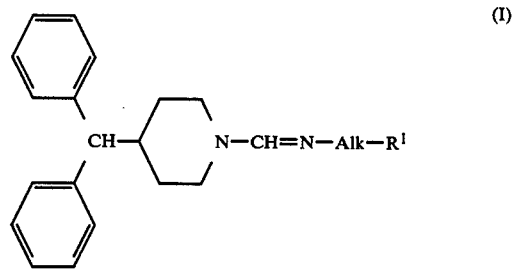

wherein

Alk is a divalent straight or branched chain alkylene unit of 1 to 12 carbons; and $R^1$ is a heterocyclic group selected from the group consisting of furan, benzofuran, thiophene or benzothiophene which heterocyclic group may be optionally substituted:
(a) on a 6-membered ring carbon thereof by one or two substituents selected from the group consisting of alkyl, alkoxy, alkylthio, hydroxy, mercapto, nitro, amino, alkylamino, dialkylamino, trifluoromethyl, alkanoylamino, halo, carboxy, carbamoyl or alkoxycarbonyl; (b) on adjacent ring carbons of the phenyl ring of the benzofuran or benzothiophene rings by a methylenedioxy group; and (c) on a carbon atom of a 5-membered ring thereof by one or two substituents selected from the group consisting of alkyl, carboxy or phenyl;
wherein said alkyl portions of the alkyl, alkoxy, alkylthio, alkylamino, dialkylamino and alkoxycarbonyl substituents contain 1 to 6 carbons and said alkanoylamino substituent contains 2 to 8 carbons, and the pharmaceutically-acceptable salts thereof.

2. The piperidine of claim 1, wherein said heterocyclic group $R^1$ is substituted by a single substituent.

3. The piperidine of claim 1, wherein said heterocyclic group $R^1$ is unsubstituted.

4. The piperidine of claim 1, wherein said heterocyclic group $R^1$ is attached to the —Alk— group by a ring carbon.

5. The piperidine of claim 1, wherein —Alk— is methylene or ethylene.

6. The piperidine of claim 1, wherein said pharmaceutically-acceptable salts are acid-addition salts.

7. The piperidine of claim 1, wherein said pharmaceutically-acceptable salts are formed with an acid selected from the group consisting of hydrohalic, sulfuric, nitric, phosphoric, acetic, propionic, glycolic, pamioc, pyruvic, oxalic, malonic, succinic, maleic, fumaric, malic, tartaric, citric, benzoic, cinnamic, mandelic, methanesulfonic, ethanesulfonic, benzenesulfonic, p-toluenesulfonic, salicylic, 2-naphthalenesulfonic or p-aminosalicylic acid.

8. The piperidine of claim 1 wherein said pharmaceutically-acceptable salts are base-addition salts.

9. The piperidine of claim 1, wherein $R^1$ is selected from the group consisting of 2-furanyl or 2-thiopheno.

10. The piperidine of claim 9, wherein —Alk—$R^1$ is selected from the group consisting of 2-furanylmethyl or 2-thiophenemethyl.

11. The piperidine of claim 1, wherein said heterocyclic group for $R^1$ is a furan.

12. The piperidine of claim 1, wherein said heterocyclic group for $R^1$ is a benzofuran.

13. The piperidine of claim 1, wherein said heterocyclic group for $R^1$ is a thiophene.

14. The piperidine of claim 1, wherein said heterocyclic group for $R^1$ is a benzothiophene.

15. A pharmaceutical composition which comprises an effective gastric acid secretion inhibiting amount of a piperidine of claim 1, in association with a pharmaceutically-acceptable carrier.

16. A method of inhibiting gastric acid secretion which comprises internally administering to a mammal in need thereof, the pharmaceutical composition of claim 15.

17. The method of claim 16 wherein said mammal is a human.

* * * * *